US00PP26665P3

(12) United States Plant Patent
Bak et al.

(10) Patent No.: US PP26,665 P3
(45) Date of Patent: Apr. 26, 2016

(54) ***MEDINILLA* HYBRID PLANT NAMED 'ROYAL INTENZ'**

(50) Latin Name: ***Medinilla* hybrid**
Varietal Denomination: ROYAL INTENZ

(71) Applicants: Elly Bak, Assendelft (NL); Nicolas Steur, Assendelft (NL)

(72) Inventors: Elly Bak, Assendelft (NL); Nicolas Steur, Assendelft (NL)

(73) Assignee: Corn Bak B.V. (NL)

( * ) Notice: Subject to any disclaimer, the term of this patent is extended or adjusted under 35 U.S.C. 154(b) by 147 days.

(21) Appl. No.: 13/999,328

(22) Filed: Feb. 10, 2014

(65) Prior Publication Data

US 2015/0230378 P1 Aug. 13, 2015

(51) Int. Cl.
*A01H 5/00* (2006.01)

(52) U.S. Cl.
USPC ..... Plt./263.1

(58) Field of Classification Search
USPC ..... Plt./263.1, 226
See application file for complete search history.

*Primary Examiner* — Annette Para
(74) *Attorney, Agent, or Firm* — Cassandra Bright

(57) ABSTRACT

A new and distinct *Medinilla* cultivar named 'ROYAL INTENZ' is disclosed, characterized by a solid growth habit, erect plant habit, measuring about 30-35 cm in height; green colored leaves, and pendulous panicles with red-purple (RHS 66A) colored flowers. The new variety is a *Medinilla,* normally produced as an ornamental plant.

2 Drawing Sheets

Figure 1:
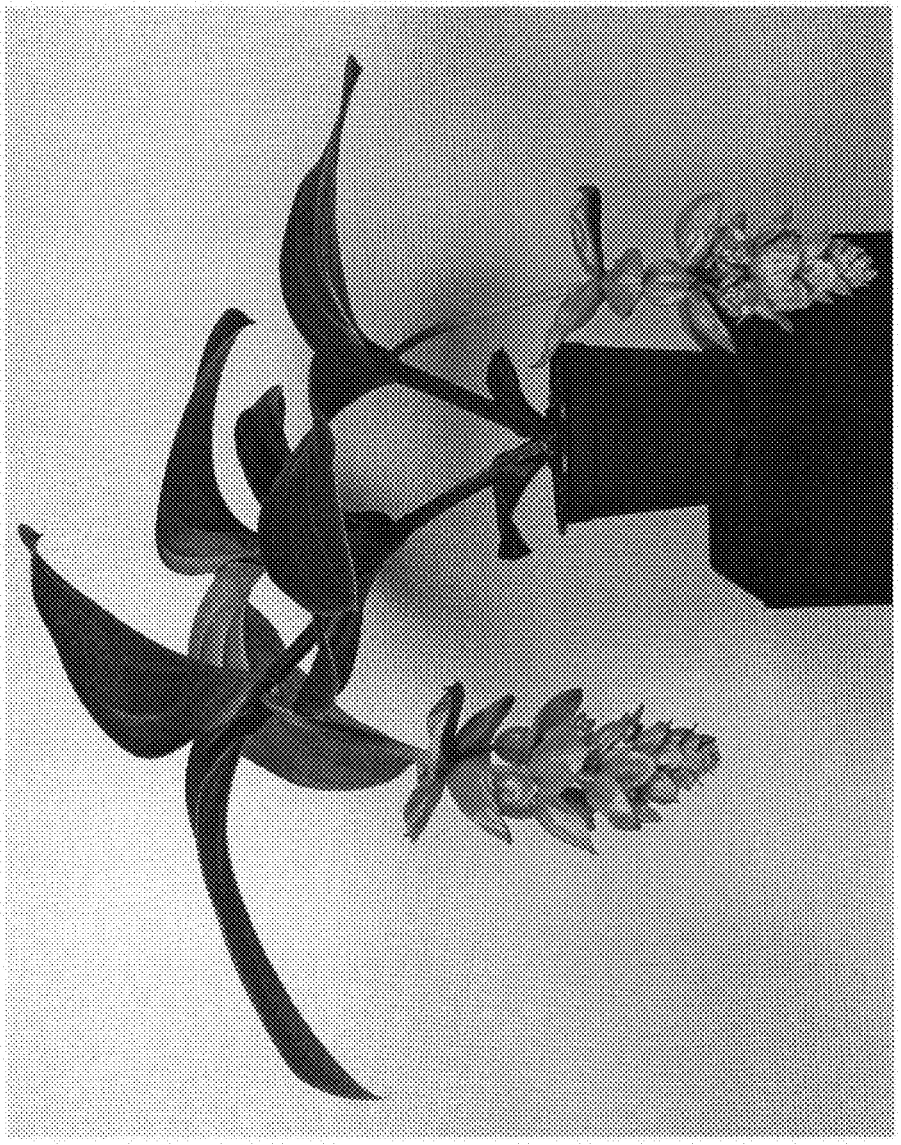

Latin name of the genus and species: *Medinilla* hybrid.
Variety denomination: 'ROYAL INTENZ'.

BACKGROUND OF THE INVENTION

The present invention relates to a new and distinct hybrid cultivar of *Medinilla* plant, botanically known as *Medinilla* sp., hereinafter referred to by the cultivar name 'ROYAL INTENZ'. The genus of *Medinilla* belongs to the Melastomataceae family.

The new *Medinilla* 'ROYAL INTENZ' is a product of a planned breeding program conducted by the inventors, Elly Black and Nico D. M. Steur, in Assendelft, The Netherlands. The objective of the breeding program was to produce new *Medinilla* variety with good growing habits and an attractive inflorescence.

The new *Medinilla* 'ROYAL INTENZ' originated from a cross made in a controlled breeding program by the inventors in 2008 in Assendelft, the Netherlands. The female or seed parent is the *Medinilla* selection designated '83198287' (unpatented), and the male or pollen parent is the *Medinilla* selection designated '83197015' (unpatented). 'ROYAL INTENZ' was discovered and selected by the inventors in 2010, as a single flowering plant within the progeny of the stated cross controlled environment in Assendelft, the Netherlands.

Asexual reproduction of the new *Medinilla* hybrid 'ROYAL INTENZ' performed by vegetative means by cuttings was first performed in 2010 Assenfeldt, the Netherlands. The first 'ROYAL INTENZ' plants propagated through the use of cuttings flowered in 2011, in Assenfeldt, The Netherlands, and have demonstrated that the combination of characteristics as herein disclosed for the new cultivar are firmly fixed and retained through successive generations of asexual reproduction. The new cultivar reproduces true-to-type.

BRIEF DESCRIPTION OF THE INVENTION

The following traits have been repeatedly observed and are determined to be the unique characteristics of 'ROYAL INTENZ' which in combination distinguish this *Medinilla* hybrid as a new and distinct cultivar:

1. Solid growth habit
2. Erect shrub plant, measuring about 30-35 cm in height (above the pot when first flowering);
3. Green colored leaves, measuring about 25-30 cm in length and about 15 cm in width;
4. Pendulous panicles with red-purple (RHS 66A) colored flowers;

Of the commercial cultivars known to the present inventors, the most similar in comparison to the new *Medinilla* 'ROYAL INTENZ' is the *Medinilla* 'BELO'(unpatented). Plants of the new *Medinilla* 'ROYAL INTENZ' differ from the plants of *Medinilla* 'BELO' primarily in inflorescence length. Plants of 'ROYAL INTENZ' have longer inflorescences than plants of 'BELO'. Additionally, plants of 'ROYAL INTENZ' have more bracts.

BRIEF DESCRIPTION OF THE PHOTOGRAPHS

The accompanying photograph illustrates the overall appearance of the new *Medinilla* 'ROYAL INTENZ' showing the colors as true as is reasonably possible with colored reproductions of this type. Colors in the photograph may differ slightly from the color values cited in the detailed botanical description which accurately describes the color of 'ROYAL INTENZ'.

FIG. 1. shows a side view perspective of a typical potted flowering plant of 'ROYAL INTENZ' at about 50 weeks from potting.

Figure 2:
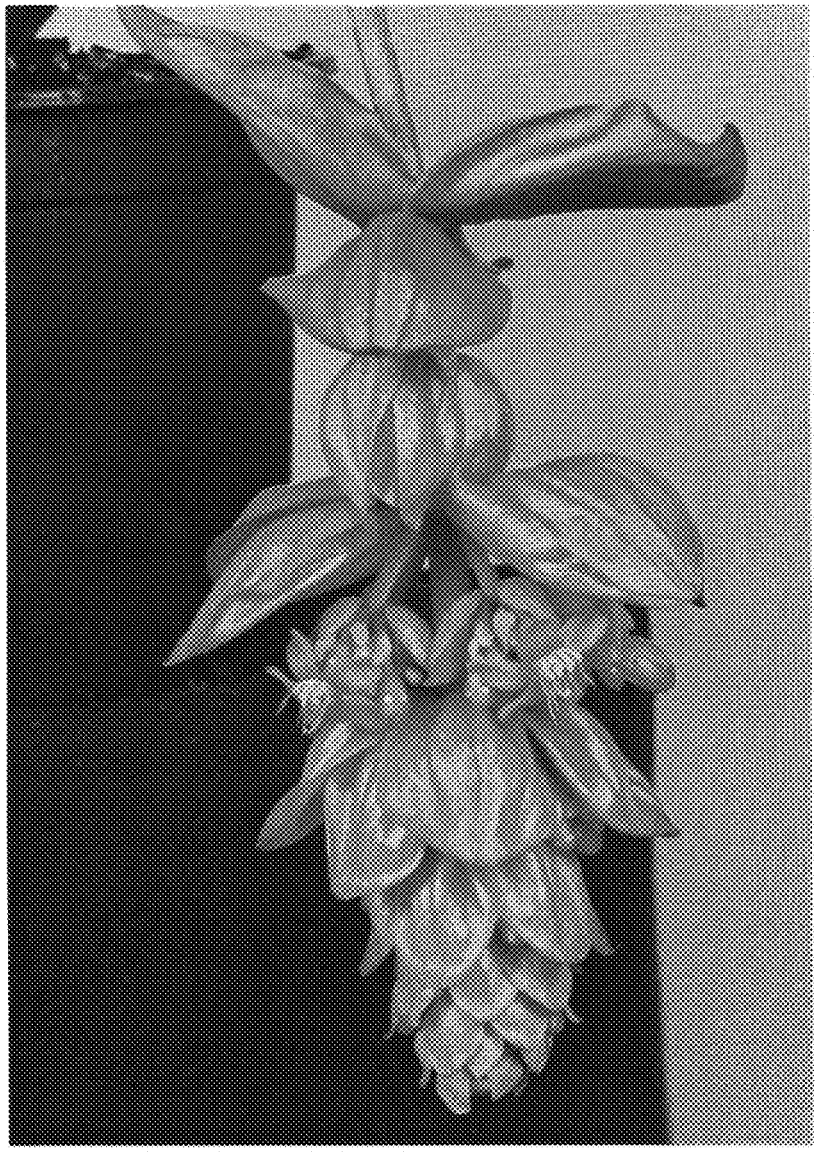

FIG. 2. shows a side view perspective of a typical flower of 'ROYAL INTENZ' at about 50 weeks from potting.

DETAILED BOTANICAL DESCRIPTION

'ROYAL INTENZ' has not been observed under all possible environmental conditions. The phenotype of the new cultivar may vary with variations in environment such as temperature, light intensity, day length, fertilizers and humidity without any change in the genotype of the plant.

The aforementioned photograph, together with the following observations, measurements and values describe the new *Medinilla* 'ROYAL INTENZ' as grown in a greenhouse in Assendelft, the Netherlands, under conditions which closely approximate those generally used in a commercial practice.

Color references are made to The Royal Horticultural Society Colour Chart (R.H.S.), 2001 Edition, except where general colors of ordinary significance are used. Color values were taken under daylight conditions in a greenhouse in Assendelft, The Netherlands. The age of the plants of 'ROYAL INTENZ' described is about 50 weeks from potting.

Botanical classification: *Medinilla* 'ROYAL INTENZ'.

Parentage:

*Female parent.*—*Medinilla* selection designated '83198287' (unpatented).

*Male parent.*—*Medinilla* selection designated '83197015' (unpatented).

Propagation: Cuttings.

Plant:

*General appearance and form.*—Height: About 30-35 cm. Diameter: About 80 cm. Shape: Erect Shrub. Growth Habit: stem. Plant Vigor: Good. Flowering Season: From April till October. Cold Tolerance: frost tender, temperatures below 5° C. may damage plants.

*Branching characteristics.*—Not very free branching.

*Quantity of primary lateral branches.*—Average: 2.

*Characteristics of primary lateral branches.*—Diameter: Lateral branches winged, average diameter 15 mm, wings typically about 3 mm. Color: Green; near RHS 143A with lignified parts near Grey-Brown 199B. Texture: Glabrous. Strength: Strong.

*Internode length.*—Average range: 7.0 cm to 16.0 cm.

Foliage:

*Arrangement.*—Opposite, attachment petiolate.

*Overall shape.*—Elliptical.

*Quantity.*—About 10.

*Average overall length.*—Average: 27.5 cm.

*Average overall width.*—Average: 15 cm.

*Apex.*—Cuspidate.

*Base.*—Acute.

*Margin.*—Slightly Undulate.

*Venation.*—Type: Parallel, sunken. Venation color upper side: Yellow-green; closest to RHS 144B. Venation color under side: Yellow-green; closest to RHS 144A.

Inflorescence:

*Size.*—Length: Average: 40 cm. Width: Average: 15 cm. Color: Red-Purple, closest to RHS 66A.

*Corolla.*—Number: Average 175.

*Petals.*—Quantity: 5 per flower. Length: Average: 13 mm. Width: Average: 8 mm. Overall Shape: Ovate, asymmetrical. Apex: Obtuse. Color: When opening, upper surface: Red-purple closest to RHS 66A. When opening, lower surface: Red-purple closest to RHS 66A.

*Sepals.*—Arrangement: Growth together, enclosing the ovary. Color, interior and exterior: Closest to RHS 66C.

*Bracts.*—Arrangement: Verticillate. Quantity: 4 per crown. Length: Average range about 1.3 cm to 8.0 cm. Width: Average range about 1.0 cm to 5.0 cm. Shape: Elliptical. Apex: Acute. Base: Truncate. Margin: Entire. Color, mature, interior: Closest to Yellow-Green 144B changing to Red 53A with age. Color, mature, exterior: Closest to Yellow-Green 144B changing to Red 53A with age. Persistent or Self-Cleaning: Self-cleaning. Fragrance: None.

*Bud.*—Shape: Obovate. Length: Average: 10 mm. Diameter: Average: 5 mm. Color: Red-purple; near RHS 64C.

*Peduncles.*—Length: Average range: 18 cm to 28 cm. Diameter: Average 8 mm. Strength: Very strong. Texture: Glabrous, matte. Color: Yellow-green; near RHS 144B near base. Changing to Red 53A closer to flower.

*Pedicels.*—Length: Average range 1.2 cm to 3.0 cm. Diameter: Average: 2 mm. Texture: Glabrous. Color: Closest to RHS Red 53D.

Reproductive organs:

*Stamens.*—Number: Average: 10. Length: Approximately 8 mm. Color: Light yellow, with a white base (too small to qualify R.H.S. value).

*Anthers.*—Shape: Length: Approximately 9 mm. Color: Violet, closest to RHS 87A, with a yellow base (too small to qualify R.H.S. value). Pollen: Not visible.

*Pistil.*—Position: Number: Average: 1 per flower. Length: Average: 18 mm. Style: Length: Color: Stigma: Shape: <1 mm. Color: white, too small to qualify R.H.S. value. Ovary: Shape: round. Position: Inferior. Length: 4 mm. Diameter: 4 mm. Color: White; closest to RHS 155C.

Other characteristics:

*Seeds and fruits.*—No seeds-fruits detected to date.

*Disease/pest resistance.*—No observations made.

*Temperature tolerance.*—Temperatures below 5 C. may damage plants.

*Drought tolerance.*—None.

What is claimed is:

1. A new and distinct cultivar of *Medinilla* plant named 'ROYAL INTENZ' as herein illustrated and described.

* * * * *